United States Patent [19]

Langer et al.

[11] 4,046,812

[45] Sept. 6, 1977

[54] PROCESS FOR PREPARING 1,1-DIMETHYL HYDRAZINE

[75] Inventors: Heimo J. Langer, Columbus; Kenneth R. Robinson; Peter E. Throckmorton, both of Worthington, all of Ohio

[73] Assignee: Ashland Oil, Inc., Ashland, Ky.

[21] Appl. No.: 617,502

[22] Filed: Sept. 29, 1975

Related U.S. Application Data

[63] Continuation-in-part of Ser. No. 510,370, Sept. 30, 1974, abandoned.

[51] Int. Cl.² ............................................. C07C 109/02
[52] U.S. Cl. ............................. 260/583 B; 260/583 N
[58] Field of Search ....................................... 260/583 B

[56] References Cited

U.S. PATENT DOCUMENTS 2,917,545  12/1959  Lum et al. ........................ 260/583 B

FOREIGN PATENT DOCUMENTS 76,520  10/1970  Germany ........................ 260/583 B

OTHER PUBLICATIONS

Adams et al., "Organic Reactions," vol. III, pp. 280–282 (1956).

*Primary Examiner*—Daniel E. Wyman
*Assistant Examiner*—John J. Doll

[57] ABSTRACT

Unsymmetrical dimethyl hydrazine is prepared by a process wherein aqueous 1,1-dimethylurea is initially reacted with a hypochlorite salt whereupon the resultant intermediate essentially in form of a N-chloro derivative of said urea is rearranged in accordance with the Hofmann reaction to yield the desired substituted hydrazine.

3 Claims, No Drawings

PROCESS FOR PREPARING 1,1-DIMETHYL HYDRAZINE

CROSS REFERENCE TO RELATED APPLICATION

This application is a continuation-in-part of application Ser. No. 510,370 filed Sept. 30, 1974, now abandoned.

BACKGROUND OF THE INVENTION

1. Field of the Invention

This invention relates to a process for the production of 1,1-dimethyl hydrazine.

2. Description of the Prior Art

Unsymmetrical dimethyl hydrazine (UDMH) is a versatile chemical intermediate having recognized usefulness in the preparation of surfactants, plant growth regulators, insecticides, dyes, monomers, etc. Currently, the largest volume use thereof is as such in the field of liquid propellants for rockets.

There presently exists two commercially adaptable methods for producing UDMH. The more desirable of these methods from the standpoint of overall efficiency involves the hydrogenation of nitrosodimethylamine in turn obtained by nitrosating dimethylamine. This method suffers because nitrosodimethylamine has been identified as such a powerful carcinogen that in order to provide an environmentally acceptable operation, an exceedingly expensive plant installation is indicated. The market for UDMH, on the other hand, is not large enough to justify such an expenditure.

The other method available for producing UDMH commercially is in accordance with the Raschig process which is based on the reaction of monochloramine with dimethylamine. This method, while presenting tedious problems associated with the recovery of the UDMH, is principally objectionable on another score in that the preparation of monochloramine can lead to the formation of trace quantities of trichloramine. The latter compound is so highly explosive that extreme care must be observed in order to assure that none of this unstable compound is produced.

It has recently been proposed to prepare UDMH by another reaction mechanism fundamentally differing from those of the aforementioned methods. Such a method, which is exemplified in East German Patent No. 76,520, is based upon the Hofmann rearrangement of 1,1-dimethylurea. The method of said patent, while environmentally acceptable and devoid of any tendency to produce hazardous or unstable compounds, is nonetheless beset with intricate processing problems. Without going into details relative to the problems involved, suffice it to say that this prior art process is difficult to implement because of the troublesome acidification of the highly basic reaction product specified therein combined with the extremely low concentration of unsymmetrical dimethylurea used. The long reaction times specified in said patent would require batch scale process equipment and consequently excessive investment costs.

In accordance with the improvement represented by the instant invention, the disadvantages associated with the prior art for converting unsymmetrical dimethylurea to UDMH can be obviated to the extent of rendering the method commercially attractive.

OBJECT OF THE INVENTION

The object of this invention is to provide a high yield process for the preparation of 1,1-dimethyl hydrazine wherein the initial integral part thereof maximizes the formation of precursor N-chlorourea derivatives for subsequent conversion in accordance with the Hofmann rearrangement reaction.

SUMMARY OF THE INVENTION

In accordance with the present invention a process is provided for the preparation of 1,1-dimethyl hydrazine wherein about equi-molar amounts of 1,1-dimethylurea and an alkali or alkaline earth metal hypochlorite are initially reacted in an aqueous system in the presence of a sufficient amount of base for stabilizing the hypochlorite salt. The foregoing reaction is conducted at a temperature of from 0° to 10° C. and in a manner whereby said urea is present in an amount which provides at least a saturated aqueous solution thereof at the given operating temperature range. The reaction mixture is thereupon basified, preferably with the same base as utilized for the stabilization of the hypochlorite salt which in turn is preferably the hydroxide of the metal cation of said hypochlorite salt. The amount of base to be added is such that when taken with base present for said stabilization purposes provide a total of two moles thereof per mole of starting urea. The basified mixture is then reacted at a temperature not in excess of 30° C. to effect the Hofmann rearrangement thereof and 1,1-dimethyl hydrazine recovered from the reaction mixture by distillation.

DESCRIPTION OF THE PREFERRED EMBODIMENTS

The reactions involved in carrying out the process to which this invention is directed are well documented in the literature. Accordingly there is no need here to indulge in any explanation of this aspect of the process since the improvement represented by the present invention basically resides in observing a combination of certain parameters in the nature of stoichiometry, reaction temperature, concentration of reactants and the mode for combining the reactants in arriving upon the final product. A detailed description of each of these critical aspects of the invention follows.

Initially, the unsymmetrical dimethylurea is combined and reacted with the selected hypochlorite salt in essentially an equi-molecular relationship. The initial phase of the reaction is effected in an aqueous medium wherein the unsymmetrical dimethylurea exists for the most part as a saturated solution in the temperature range contemplated for this portion of the process. This reaction concentration can be most conveniently expressed in terms of molal concentration; meaning the number of gram moles of the dimethylurea in one kilogram of water at about room temperature. Accordingly, the applicable lower molal concentration of the dimethylurea is in the order of two, at which concentration the urea will exist essentially as a saturated solution within the contemplated reaction temperature range. More preferably, however, the molal concentration of the dimethylurea is in the order of about three, in which case this reactant will exist as a relatively fluid slurry of the urea in a saturated solution thereof. Higher molal concentrations can be used with the limiting factor being that of the processing capability of the reactor equipment utilized.

Any of the alkali or alkaline earth metal hypochlorites can be reacted with the unsymmetrical dimethylurea in the initial phase of the reaction. Of such salts, however, sodium hypochlorite is preferred. Aqueous solutions of the aforesaid hypochlorites are readily prepared by passing chlorine through an aqueous solution of the selected base. Since the formation of the hypochlorite salt in this manner is an equilibrium reaction, one will only obtain that concentration of the salt which is inherently stable toward decomposition. Stable solutions will accordingly contain free base, the amount of which in turn depends on the particular equilibrium constants involved. For all of the indicated metals this amount of free base will be less than one mole per mole of the hypochlorite salt present in the solution. The precise amount of base present in stable solutions of this type depends on the cation portion of the system. As regards the preferred cation; namely, sodium, the amount of caustic present in stable solutions is about 0.7 mole thereof per mole of the sodium hypochlorite.

The minimum molal concentration of the hypochlorite solution corresponds to that specified for the dimethylurea solution. Preferably, however, a molal concentration of this reactant is in the order of about three, irrespective of using solutions of the urea at a lower concentration. Notwithstanding such optional use of different concentrations for these reactants, they must be combined in an essentially equi-molecular relationship.

The temperature in observing the reaction between the dimethylurea and hypochlorite salt is of a critical nature and ranges from about 0° to 10° C. and more preferably not in excess of about 5° C. A reaction temperature in excess of the maximum specified is to be avoided because of the adverse effect of such higher temperatures in leading to the formation of yield-reducing by-products. The reaction between the urea and hypochlorite is highly exothermic and thus cooling is called for as a practical expedient in order to maintain the reaction temperature within the aforesaid range. Essentially, the reaction yields the N-chloro derivative of the substituted urea which formation occurs extremely rapidly, usually in a matter of minutes. Following the completion of the reaction between the hypochlorite and urea, the aqueous reaction mixture is then basified in order to effect the rearrangement thereof in accordance with the Hofmann reaction. This rearrangement is facilitated by observing a higher temperature but not to exceed about 30° C. The preferred temperature for effecting rearrangement is from about 20° to 25° C. The amount of base utilized in this phase of the process when taken together with the amount of base present in the initial reaction mixture is two moles per mole of the starting unsymmetrical dimethylurea. Desirably the added base should be the hydroxide of the starting hypochlorite solution. The overall reaction mechanism occurring in the rearrangement is completed when the active chlorine content of the reaction mixture is reduced to essentially nil. The standard test for determining active chlorine via titration with sodium thiosulfate is applicable. The rearrangement reaction like that in forming the N-chloro derivatives of the starting urea is relatively rapid and under the preferred operating conditions specified herein will completely run its course within 10 minutes or less. The unsymmetrical dimethyl hydrazine can thereupon be conveniently recovered by way of distillation conducted under vacuum or at ambient pressure conditions.

The process of this invention can be carried out in a batch or by the continuous method of operation. High yields of unsymmetrical dimethyl hydrazine can be obtained by either method; however, the process of the invention is ideally suited for carrying out in a continuous manner. This is so because the reaction rates experienced in both phases of the process are very rapid and moreover, the exotherm experienced in the initial reaction can be most conveniently controlled.

In order to illustrate the invention the following working examples are set forth. Beyond describing the best mode contemplated for implementing the invention these examples are given solely for the purpose of illustration. Accordingly, any enumeration of detail contained therein is not to be necessarily construed as limitations on the invention. The only limitations intended are those expressed in the appended claims. All parts specified are parts by weight unless otherwise qualified.

EXAMPLE I

Into a 250 ml three neck flask equipped with a thermometer, stirrer, reflux condenser and addition funnel was charged 8.8 g. (0.1 mole) of 1,1-dimethylurea dissolved in 50 g. water. The stirred solution was cooled to 0° C. and a 15.8 weight % solution of sodium hypochlorite in the amount of 47.2 g. (0.1 mole NaOCl) containing 5.9 weight % (0.07 mole) sodium hydroxide was added within 3 to 5 minutes while maintaining the temperature at 0°-2° C. Following the exothermic peak experienced upon completion of the hypochlorite solution addition, 5.2 g. (0.13 mole) of sodium hydroxide was added in the form of a 20% aqueous caustic solution. With continued stirring the reaction mixture was permitted to rise to about 5° C. and held for 8 minutes. The reaction mixture was then split into parts and the unsymmetrical dimethyl hydrazine was recovered by distillation. In one instance, distillation was accomplished under atmospheric conditions and in the other under vacuum (21-25 mm Hg.). The distillation carried out under atmospheric conditions yielded 83.5% unsymmetrical dimethyl hydrazine; whereas, distillation under vacuum yielded 85% of product, both yield figures based on theory. The indicated yields were determined by GLC analysis.

EXAMPLE II

In this example a series of experimental runs were conducted for the purpose of illustrating the effect in terms of observed yields of certain variables such as the combining ratio of reactants, temperature during the initial reaction step, etc. The procedure was identical to that observed in Example I with respect to operative features. Other relevant data with respect to these runs and the results obtained are given in the following Table I. Reactant amounts set forth therein are given on a molar basis.

TABLE I

| Run No. | DMU[1] | NaOCL | NaOH[2] | TEMP.[3] ° C | Yield % |
|---------|--------|-------|---------|--------------|---------|
| 1 | 0.1 | 0.1 | 0.2 | 0 | 83.0 |
| 2 | 0.1 | 0.1 | 0.2 | 10 | 62.5 |
| 3 | 0.1 | 0.1 | 0.2 | 20 | 51.7 |
| 4 | 0.1 | 0.1 | 0.2 | 30 | 27.0 |
| 5 | 0.2 | 0.29 | 0.3 | 0-2 | 55.6 |
| 6 | 0.1 | 0.10 | 0.11 | 0 | 54.0 |
| 7 | 0.1 | 0.10 | 0.08 | 10 | 48.0 |
| 8 | 0.1 | 0.10 | 0.07 | 20 | 48.2 |

[1]DMU - 1,1-dimethylurea
[2]Total amount of base
[3]Temperature during the addition of the NaOCl

EXAMPLE III

This example illustrates the preparation of unsymmetrical dimethyl hydrazine by the process of this invention conducted in a continuous manner.

A metered stream of 2.96 g./min. of 20.0% aqueous 1,1-dimethylurea (6.67 mmol/min.) was mixed at 0°-2° C. with a metered stream of 3.02 g./min. of a hypochlorite solution containing 16.5% NaOCl. (6.67 mmol/min.) and 4.4% NaOH (3.33 mmol/min) in a first stage reactor comprising ⅛ inch O.D. stainless steel tubing of 2.0 ml volume followed by a stainless steel tube of ¼ inch O.D. and having a volume of 42 ml. The first-stage reactor was maintained at 0°-2° C. by immersion in ice water. The effluent from the indicated reactor was then mixed with 2.00 g/min. of a metered stream of 20.0% aqueous sodium hydroxide (10.0 mmol/min.). The basified stream was fed into a second-stage reactor identical to that of the first-stage reactor except for the ¼ inch length of tubing. The reaction temperature in the second stage reactor was maintained at 23°-25° C. by immersion in a water bath. The effluent from the second-stage reactor was run into a 500 ml. distillation stage at a pot temperature of 104°-8° C. Aqueous 1,1-dimethyl hydrazine distillate was produced continuously at a rate of 4.37 g./min. Over a 47 minute period the average concentration of dimethyl hydrazine in the distillate stream was 6.8%, equivalent to 5.0/mmol/min. rate of 100% 1,1-dimethyl hydrazine or 75.1% of the theoretical rate. Fractionation yielded 99.0% 1,1-dimethyl hydrazine bp. 62.5°-3.5° C. In the foregoing run the residence times were 9.07 and 6.47 minutes for the first-stage reactor and second-stage reactor, respectively.

What is claimed is:

1. A process for the preparation of 1,1-dimethyl hydrazine which comprises initially reacting in an aqueous medium at a temperature of from 0° to 10° C about equi-molar amounts of 1,1-dimethylurea and an alkali or alkaline earth metal hypochlorite, said hypochlorite salt associated with $x$ mole of a corresponding metal hydroxide where $x$ is less than one mole per mole of the hypochlorite salt but in a sufficient amount to inhibit substantially completely the decomposition thereof, and wherein the concentration of each reactant is at least about 1.0 molal, thereupon introducing an additional amount of said metal hydroxide to provide (2-$x$) moles thereof per mole of the starting 1,1-dimethylurea and reacting the basified mixture at a temperature not in excess of 30° C to effect the rearrangement thereof whereupon 1,1-dimethyl hydrazine is recovered by distillation.

2. A process for the preparation of 1,1-dimethyl hydrazine which comprises combining about a 3 molal aqueous solution of 1,1-dimethylurea with a like molal aqueous solution of sodium hypochlorite containing about 0.7 mole sodium hydroxide per mole of the sodium hypochlorite and reacting at a temperature between 0° and 10° C, thereupon adding 1.3 moles of sodium hydroxide per mole of said sodium hypochlorite as a 20 weight percent aqueous solution of said base and reacting the basified mixture at temperature of from about 10°-30° C to effect the rearrangement thereof whereupon 1,1-dimethyl hydrazine is recovered by distillation.

3. A process in accordance with claim 2 wherein said first-named reaction temperature range is between 0° and 5° C and said second-named reaction temperature range is between about 20° and 25° C.

* * * * *